(12) United States Patent
Eyjolesson

(10) Patent No.: US 7,045,511 B2
(45) Date of Patent: May 16, 2006

(54) FOSINOPRIL FORMULATION

(75) Inventor: Reynir Eyjolesson, Hafnarfjordur (IS)

(73) Assignee: Actavis Group HF., Hafnarfjordur (IS)

( * ) Notice: Subject to any disclaimer, the term of this patent is extended or adjusted under 35 U.S.C. 154(b) by 92 days.

(21) Appl. No.: 10/507,918

(22) PCT Filed: Mar. 19, 2003

(86) PCT No.: PCT/IS03/00013

§ 371 (c)(1),
(2), (4) Date: Sep. 16, 2004

(87) PCT Pub. No.: WO03/077929

PCT Pub. Date: Sep. 25, 2003

(65) Prior Publication Data

US 2005/0256086 A1 Nov. 17, 2005

(30) Foreign Application Priority Data

Mar. 19, 2002 (IS) .......................................... 6315

(51) Int. Cl.
*A61K 31/675* (2006.01)

(52) U.S. Cl. ..................................................... 514/91

(58) Field of Classification Search .................... None
See application file for complete search history.

(56) References Cited

U.S. PATENT DOCUMENTS

| 4,337,201 | A | * | 6/1982 | Petrillo, Jr. ................. 548/413 |
| 5,006,344 | A | | 4/1991 | Jerzewski et al. |
| 2002/0131999 | A1 | | 9/2002 | Sherman |
| 2003/0109557 | A1 | * | 6/2003 | Foster ........................ 514/355 |
| 2005/0037068 | A1 | * | 2/2005 | Massironi ................... 424/464 |
| 2005/0070557 | A1 | * | 3/2005 | Fryburg et al. .......... 514/262.1 |

OTHER PUBLICATIONS

Gu, L. et al., "Drug-excipient Incompatibility Studies of the Pipeptide Angiotensin-Converting Enzyme Inhibitor, Moexipril Hydrochloride: Dry Powder Vs. Wet Granulation," *Pharmaceutical Research*, vol. 7, No. 4, pp. 379-383 (Apr. 1990).

Al-Omari, M. et al., "Effect of the Drug-Matrix on the Stability of Enalapril Maleate in Tablet Formulations," *Journal of Pharmaceutical and Biomedical Analysis*, vol. 25, No. 5-6, pp. 893-902 (Jul. 2001).

* cited by examiner

*Primary Examiner*—Raymond J. Henley, III
(74) *Attorney, Agent, or Firm*—Wenderoth, Lind & Ponack, L.L.P.

(57) ABSTRACT

A pharmaceutical formulation is provided comprising fosinopril which is the prodrug of an angiotensin converting enzyme (ACE) inhibitor, fosinoprilat. The formulation is characterized by comprising in the range of about 0.25 to about 5% glyceryl dibehenate which has been found to be a highly useful lubricant in the manufacture of tablets according to the present invention, enhancing the stability of fosinopril as compared to prior art formulations.

9 Claims, No Drawings

FOSINOPRIL FORMULATION

FIELD OF INVENTION

The present invention is within the field of pharmaceuticals, particularly relating to improved formulations of the ACE inhibitor prodrug fosinopril.

TECHNICAL BACKGROUND AND PRIOR ART

Fosinopril is the ester prodrug of an angiotensin converting enzyme (ACE) inhibitor, fosinoprilat. The compound can be used as an antihypertensive agent. Its ability to inhibit ACE and thus lower blood pressure is disclosed in U.S. Pat. No. 4,337,201. The compound (the sodium salt, which is the commonly used drug form) is designated chemically as L-proline 4-cyclohexyl-1-[[[2-methyl-1-(1-oxopropoxy)propoxy](4-phenylbutyl)phosphinyl]acetyl]sodium, trans-, see Formula (I).

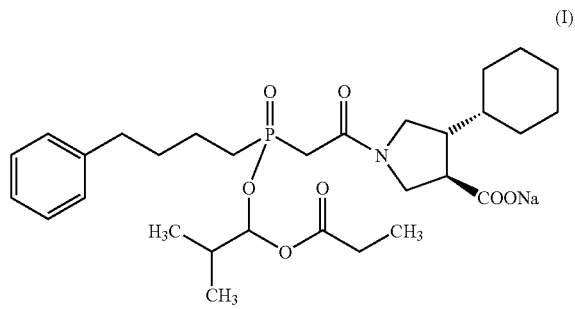

The prodrug is converted in vivo into the active component by hydrolysis of the diester sidechain. Fosinopril sodium has a relatively low bulk density, exhibits poor flow characteristics, and adheres to metal surfaces during tableting. Fosinopril has been tableted by a wet granulation process using magnesium stearate as a lubricant material. Tablets produced from such blend have low stability, are moisture sensitive and require the use of a protective package for a useful shelf life.

U.S. Pat. No. 5,006,344 suggests the use of sodium stearyl fumarate or hydrogenated vegetable oil instead of magnesium stearate, to increase the stability of fosinopril tablets. The reference however, does not discuss why the two preferred lubricants are found to be better than magnesium stearate, or suggest other possible lubricants. It has been suggested that the degradation of fosinopril in Mg stearate compositions is due to the effect of the Mg metal ion (Thakur, A. B. et al. Pharm. Res. 10 (6) 800–809 (1993)).

It has now been found that fosinopril sodium tablets comprising glyceryl dibehenate as lubricant have excellent stability. Glyceryl dibehenate has several advantages when used in fosinopril compositions as compared to other lubricants used in prior art compositions. In contrast to salts of fatty acids and fatty acid derivatives including magnesium stearate or sodium stearyl fumarate, glyceryl dibehenate is a neutral and non-metal containing compound.

In contrast to hydrogenated vegatable oil, glyceryl dibehenate is chemically a clearly defined substance and can be obtained with a well defined particle size.

SUMMARY OF INVENTION

The present invention provides a pharmaceutical formulation comprising in the range of about 1% to 25% fosinopril or a salt thereof, the formulation being characterized by comprising in the range of about 0.25 to about 5% glyceryl dibehenate.

DETAILED DESCRIPTION

The present formulation is particularly useful in tablet formulations, however, it is as well contemplated that the formulations according to the invention can be formulated for capsules, sachets, caplets or other solid dosage forms. As mentioned the formulation comprises in the range of about 1% to 25% fosinopril or a related salt thereof, preferably the sodium salt, such as about 1–10%, including about 1–5%. The formulation is characterized by comprising in the range of about 0.25 to about 5% glyceryl dibehenate, such as in the range of about 0.5–5%, or about 1–5%, e.g. in the range of about 1–2.5%, including about 1%, and about 2%, or about 2.5% of glyceryl dibehenate. All percentages used herein refer to weight percentages if not otherwise noted.

Glyceryl dibehenate may be obtained by esterification of glycerol with behenic acid (C 22:0 fatty acid). The product is provided commercially by Gattefossé s.a. under the tradename Compritol 888 ATO. Compritol has a fatty acid composition with over 83% benehic acid, 40–60% of the fatty acids are in diester form (diglycerides), and 21–35% are in triester form (triglycerides). Accordingly, useful embodiments of the invention comprise a lubricant formulation in the above amount comprising in the range of about 50–100 wt % of glyceryl di-and tribehenate, such as in the range of about 55–95 wt %, including the range of about 70–80 wt %. Such lubricant formulations would generally contain glyceryl dibehenate and glyceryl tribehenate in a ratio ranging from about 1:1 to about 3:1.

The formulation of the present invention typically further comprises conventional excipients such as a filler, a disintegrant, and a binder. In one embodiment the formulation comprises in the range of 30 to 85% of a filler substance, which may be one of numerous substances generally known in the art, such as e.g. a saccharide (e.g. lactose or mannitol) or microcrystalline cellulose or a mixture thereof, and may further comprise in the range of 0.5 to 5 wt % of a disintegrant such as crosslinked sodium carboxymethylcellulose (NaCMC), crosslinked polyvinylpyrrolidone or mixtures thereof. Suitable binders include povidone (2-pyrrolidinone), hydroxypropyl cellulose, pregelatinized starch, gelatin and mixtures thereof. The formulations may additionally comprise other commonly used excipients that are compatible with the active ingredient such as pigments, colorants, sweeteners, taste-masking agents and the like.

For production of tablets a direct compression or wet granulation process may be used, where the latter is presently preferred.

In certain embodiments the formulation of the invention further comprises in the range of about 0.5–50 wt % of a pharmaceutically active compound selected from the group containing diuretics including hydrochlorothiazide; antitussives including dextromethorphan, dextromethorphan hydrobromide, noscapine, carbetapentane citrate, and chlophedianol hydrochloride; antihistamines including chlorpheniramine maleate, phenindamine tartrate, pyrilamine maleate, doxylamine succinate, and phenyltoloxamine citrate; decongestants including phenylephedrine hydrochloride, phenylpropanolamine hydrochloride, pseudoephedrine hydrochloride, ephedrine; and alkaloids such as codeine phosphate, codeine sulfate, and morphine.

The following non-limiting examples illustrate in more detail a preferred embodiment of the invention and its advantages.

EXAMPLES

Example 1

The following materials were combined by wet granulation to produce 5 mg, 10 mg, and 20 mg fosinopril sodium tablets (tablet weight 100 mg, 200 mg, 200 mg respectively):

| | | | |
|---|---|---|---|
| Fosinopril sodium | 5.0 mg | 10.0 mg | 20.0 mg |
| Lactose monohydrate | 59 mg | 118 mg | 108 mg |
| Starch, pregelatinized (starch 1500) | 12 mg | 24 mg | 24 mg |
| Crosslinked NaCMC (croscarmellose sodium) | 2 mg | 4 mg | 4 mg |
| Water, purified | q.s. | q.s. | q.s. |
| Microcrystalline cellulose | 20 mg | 40 mg | 40 mg |
| Glyceryl dibehenate* | 2 mg | 4 mg | 4 mg |

*Compritol ™ 888 ATO, Gattefossé s.a., France

Example 2

Stability of tablets prepared in Example 1 and of marketed preparation were tested at 40° C. for one month. Hydrolysis of fosinopril into fosinoprilat was assayed and measured as relative amount of initial amount of fosinopril.

| | Assay | Fosinoprilat |
|---|---|---|
| Tablets from Ex. 1 | 4.9 mg | 1.7% |
| Marketed prepn**. | 4.9 mg | 2.6% |

**Dynacil ™ fosinopril sodium 5 mg tablets, containing sodium stearyl fumarate as lubricant The example demonstrates a surprisingly good stability of fosinopril sodium tablets according to the present invention.

Example 3

The following materials are combined by wet granulation to produce tablets with 10 mg fosinopril sodium and 12.5 mg hydrochlorothiazide (tablet weight 200 mg):

| | |
|---|---|
| Fosinopril sodium | 10.0 mg |
| Hydrochlorthiazide | 12.5 mg |
| Lactose monohydrate | 105.5 mg |
| Starch pregelatinized | 24 mg |
| Crosslinked NaCMC | 4 mg |
| Water purified | q.s. |
| Microcrystalline cellulose | 40 mg |
| Glyceryl dibehenate | 4 mg |

The invention claimed is:

1. A pharmaceutical formulation comprising in the range of about 1% to 25% fosinopril or a salt thereof, the formulation characterized by comprising glyceryl dibehenate as a lubricant agent.

2. The formulation of claim 1 comprising the sodium salt of fosinopril.

3. The formulation of claim 1 comprising in the range of about 0.25 to about 5% glyceryl dibehenate.

4. The formulation of claim 1 formulated in tablet dosage form.

5. The tablet formulation of claim 4 produced by wet granulation.

6. The formulation of claim 1 further comprising in the range of 30 to 85 wt % of a filler substance, and in the range of 0.5 to 5 wt % of a disintegrant such as crosslinked sodium carboxymethylcellulose.

7. The formulation of claim 1 comprising about 5 wt % fosinopril sodium, about 2 wt % of a lubricant formulation comprising in the range of about 50–100 wt % glyceryl di- and tribehenate, in the range of about 50–70 wt % lactose monohydrate, about 20 wt % microcrystalline cellulose, and about 2 wt % croslinked sodium carboxymethylcellulose.

8. The formulation of claim 1 further comprising 0.5–50 wt % of a pharmaceutically active compound selected from the group containing diuretics including hydrochlorothiazide; antitussives including dextromethorphan, dextromethorphan hydrobromide, noscapine, carbetapentane citrate, and chlophedianol hydrochloride; antihistamines including chlorpheniramine maleate, phenindamine tartrate, pyrilamine maleate, doxylamine succinate, and phenyltoloxamine citrate; decongestants including phenylephedrine hydrochloride, phenylpropanolamine hydrochloride, pseudoephedrine hydrochloride, ephedrine; and alkaloids such as codeine phosphate, codeine sulfate, and morphine.

9. The formulation of claim 8 comprising 0.5–50 wt % of hydrochlorothiazide.

* * * * *

UNITED STATES PATENT AND TRADEMARK OFFICE
CERTIFICATE OF CORRECTION

| | | |
|---|---|---|
| PATENT NO. | : 7,045,511 B2 | |
| APPLICATION NO. | : 10/507918 | |
| DATED | : May 16, 2006 | |
| INVENTOR(S) | : Reynir Eyjolfsson | |

It is certified that error appears in the above-identified patent and that said Letters Patent is hereby corrected as shown below:

On Title Page,

Item (75) the Inventor's name, "Reynir Eyjolesson," should read
-- Reynir Eyjolfsson, --.

Signed and Sealed this

Thirtieth Day of January, 2007

JON W. DUDAS
*Director of the United States Patent and Trademark Office*